United States Patent
Rorrer, III et al.

(10) Patent No.: US 8,049,167 B2
(45) Date of Patent: Nov. 1, 2011

(54) PNEUMATIC ION BEAM FOCUSING IN HIGH-FIELD ASYMMETRIC WAVEFORM ION MOBILITY SPECTROMETRY (FAIMS)

(75) Inventors: Leonard C. Rorrer, III, Gainesville, FL (US); Richard Alan Yost, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 125 days.

(21) Appl. No.: 12/723,066

(22) Filed: Mar. 12, 2010

(65) Prior Publication Data

US 2010/0264306 A1    Oct. 21, 2010

Related U.S. Application Data

(60) Provisional application No. 61/159,986, filed on Mar. 13, 2009.

(51) Int. Cl.
 *H01J 49/40* (2006.01)

(52) U.S. Cl. ........................................................ 250/286
(58) Field of Classification Search .................. 250/286, 250/287, 281, 282
See application file for complete search history.

(56) References Cited

U.S. PATENT DOCUMENTS

| | | | | |
|---|---|---|---|---|
| 7,135,674 B2 * | 11/2006 | Guevremont et al. | ........ | 250/288 |
| 7,189,966 B2 * | 3/2007 | Syms | ............................ | 250/292 |
| 7,638,765 B1 * | 12/2009 | Belford et al. | ................ | 250/290 |

* cited by examiner

*Primary Examiner* — Kiet Nguyen
(74) *Attorney, Agent, or Firm* — Saliwanchik, Lloyd & Eisenschenk

(57) ABSTRACT

A FAIMS device for separating ions has a pair of electrodes for providing a compensation voltage and an asymmetric waveform that are separated and insulated where at least one porous spacer reside in the proximity of the analyzer region of the FAIMS cell. The porous spacers allow a focusing gas to flow into the analyzer region to provide pneumatic focusing of the ions traversing the analyzer region to improve the ion transmission.

20 Claims, 5 Drawing Sheets

PNEUMATIC ION BEAM FOCUSING IN HIGH-FIELD ASYMMETRIC WAVEFORM ION MOBILITY SPECTROMETRY (FAIMS)

CROSS-REFERENCE TO RELATED APPLICATION

The present application claims the benefit of U.S. Provisional Application Ser. No. 61/159,986, filed Mar. 13, 2009, which is hereby incorporated by reference herein in its entirety, including any figures, tables, or drawings.

The subject invention was made with government support under a research project supported by the National Science Foundation, subcontract from Washington State University, Contract No. CBET-0731306. The government has certain rights to this invention.

BACKGROUND OF THE INVENTION

Ion mobility spectrometry (IMS) is an important technique for the detection of narcotics, explosives, and chemical warfare agents because of its high sensitivity and amenability to miniaturization for field-portable applications. In IMS, gas-phase ions migrate in a drift tube in the presence of a constant electric field. Ions are separated by differences in their drift velocities. For electric field strengths that are relatively low, an ion's drift velocity depends on the applied electric field strength and the mobility, K, which is independent of the applied electric field and experimentally determined. The ions travel through a bath gas at a sufficiently high pressure that allows the ions to rapidly achieve a constant velocity when driven by the force of a constant electric field, which contrasts to migration in a mass spectrometer where ions accelerate in a constant electric field at low pressure.

At high electric field strengths the ion drift velocity is not directly proportional to the applied field and the mobility, $K_h$, is not a constant, but rather dependent on the applied electric field. This dependence has been exploited to develop high field asymmetric waveform ion mobility spectrometry (FAIMS) where ions are separated by a difference in their mobility at high field strength, $K_h$, relative to their mobility at low field strength, K. In FAIMS, ions are separated due to the dependent behavior of $K_h$ as a function of the applied electric field strength.

A FAIMS spectrometer has an analyzer region defined by the space between two electrodes. One electrode is maintained at a selected dc voltage, often at ground potential, while the second electrode has an asymmetric waveform V(t) imposed upon it that is a repeating pattern of a short, $t_h$, high voltage, $V_h$, periods and longer, $t_l$, lower voltage, $V_l$, periods such that $V_h t_h + V_l t_l = 0$ for each complete cycle of the waveform. The peak voltage during the high voltage portion of the waveform is called the "dispersion voltage" or DV.

Ions to be separated are entrained in a stream of gas flowing through the FAIMS analyzer region. The net motion of an ion is the sum of an axial x-axis component due to the stream of gas and a transverse y-axis component due to the applied electric field. The distance traveled by an ion during the high voltage portion of the waveform is given by $d_h = K_h E_h t_h$ where $E_h$ is the applied field. During the low voltage portion of the asymmetric waveform, $d_l = K E_l t_l$. As $E_h t_h$ and $E_l t_l$ are equal in magnitude the net displacement along the y-axis occurs because of the difference in $K_h$ and K. This transverse drift is compensated by applying a constant voltage to the first electrode, the "compensation voltage" or CV. Hence, where multiple ions are present, only an ion whose drift is compensated can arrive at a detector for an appropriate combination of DV and CV. Analysis can be carried out by changing CV over time.

Buryakov et al. *Int. J. Mass Spectrom. Ion Processes*, 128, 143 (1993) disclosed the first FAIMS device with planar electrodes. The electric field between the planar electrodes is uniform, allowing ions to diffuse laterally. Because there is a lack of ion focusing, poor ion transmission into the narrow outlet, which is often the entrance to a mass spectrometer, affects sensitivity. The use of curved electrodes produces a two-dimensional atmospheric pressure ion focusing effect that achieves greater ion transmission efficiencies. For example, Carnahan et al. U.S. Pat. No. 5,420,424, describes a device where two cylindrical electrodes are used where one electrode is concentrically located within a tubular electrode and the ions are transmitted parallel to the central axis of the cylinders. Guevremont et al., WO 00/08455, describe a domed-FAIMS analyzer where a cylindrical inner electrode has a curved surface terminus proximate an ion outlet orifice to an analyzer region. The application of an asymmetric waveform to the inner electrode has an additional ion-focusing action that extends around the spherically shaped terminus of the inner electrode that causes the selected ions to be directed radially inwardly within the region proximate the inner electrode terminus. Guevremont et al., WO 1/69216 disclose a "side-to-side" FAIMS. In this design the ions are transmitted around the circumference of an inner cylindrical electrode. The ion inlet and the ion outlet of a side-to-side FAIMS device are disposed, one opposing the other, within a surface of the outer electrode. An ion is selectively transmitted through the curved analyzer region between the ion inlet and the ion outlet along a continuously curving ion flow path perpendicular to the central axis of the cylinders. The ions travel approximately fifty percent of the circumference of the inner electrode and are partitioned between two streams traveling in opposite directions around the inner electrode, effective reducing the ion density within the analyzer region, reducing the ion-ion repulsion space charge effect, and allowing a reduction of the travel distance to improve the ion transmission efficiency. However, in this design the ions are not focused in a direction parallel to the central axis of the cylindrical electrodes and an inner cylinder with a small radius is required to produce a strongly focused field, which can result in ion transit times that can be insufficient to separate mixtures of different ions.

Both planar and cylindrical ("dome" and "side-to-side") geometries have been used for commercial FAIMS systems: the DMS (Sionex, Bedford, Mass.); and Selectra (Ionalytics, Ottawa, Canada). These commercial systems are used for detection of drugs, explosives, chemical warfare agents, environmental monitoring, bacterial typing, product quality assurance, natural resource management, and biomedical research. However, the use of FAIMS has often been limited by resolving power ($R_p$) which is about an order of magnitude less than that of the Ion Mobility Spectrometry (IMS) designs.

Shvartsburg et al., *Anal Chem.* 2006, 78(11), 3706-14 has compared the inherent resolving power of simulated planar and cylindrical FAIMS systems. As one proceeds from a curved surface of 8 mm with a $R_p$ of 10 to a curved surface of 73 mm with an $R_p$ of 45, the ion transmission suffers from 96% at $R_p$=10 to 2% at $R_p$=45. At higher curvatures, approaching ∞ for a planar surface, although $R_p$ should increase significantly, the ion transmission would become insufficient for practical use. One critical difference between planar and cylindrical FAIMS is in the dependence of peak widths on the ion residence time. In a cylindrical system, ions with CVs outside of a finite range are filtered out, allowing equilibrium in the gap that requires a certain residence time (~50 ms for the commercial Selectra), and greater FAIMS resonance time does not improve resolution. In planar systems a single CV permits ion equilibrium and ions with even a small CV difference will eventually be eliminated with sufficient time. Hence, longer separation times would increase $R_p$ (in principle) indefinitely. However, longer residence time can further diminishes the ion transmission due to lateral diffusion. Commercial planar systems typically have a residence time that is about two orders of magnitude less than that of a cylindrical system to have similar ion transmission. Tang et al., U.S. Patent Application Publication 2007/020059 discloses the use of an "ionic funnel" at a non circular ion outlet of a planar FAIMS unit where an ion transmission of more than two fold was displayed because virtually no loss is experienced between the outlet from the FAIMS ion outlet and the outlet of the "ionic funnel."

Hence, it would be advantages to use FAIMS units that can increase the resolving power if better or additional means of diminishing the effects of lateral diffusion of the ions in the analyzer region could be achieved to improve ion transmission.

BRIEF SUMMARY OF THE INVENTION

Embodiments of the invention are directed to apparatus for separating ions having one or more ion inlets and one or more ion outlets situated at the ends of an analyzer region defined by the volume between constantly displaced opposing surfaces of a first electrode and a second electrode that are electrically insulated from each other with at least one porous spacer addressing the analyzer region. Electrical contact is made to at least one of the electrodes for applying a compensation voltage between the electrodes and an electrical contact is also made to at least one of the electrodes for applying an asymmetric waveform. By application of the compensation voltage and asymmetric waveform, one or more ions can be selectively transmitted from an ion inlet through the analyzer region to an ion outlet. At least one gas source is included to provide a focusing gas that diffuses through the porous spacers to focus the ions pneumatically.

The porous spacer can be constricted of a porous plastic, porous glass, sintered ceramic, sintered glass, microperforated anodized aluminum, or microperforated plastic. The porous spacer can have an effectively uniform porosity or can have different porosities at different portions of the porous spacer. The focusing gas or gases can be an inert gas, a reactive gas or a reactive gas diluted by an inert gas. The focusing gas pressure can differ at different portions of the porous spacer, which can be constructed as an ensemble of porous spacer segments that can be independently addressed by one or more gas source.

In one embodiment of the invention, opposing surfaces of the first and said second electrodes are parallel and flat with the pair of porous spacers situated between the opposing surfaces of the electrodes on opposing sides of the analyzer region. In another embodiment of the invention the first electrode has an outer cylindrical surface and is situated around the second electrode that has an opposing coaxial inner cylindrical surface with the pair of porous spacers situated between the electrodes on opposing sides and parallel to the analyzer region. In another embodiment of the invention, the first electrode is an outer electrode having an inner concave partial ovoidal surface and the second electrode is an inner electrode with an outer concave partial ovoidal surface, where the convex and concave partial ovoidal surfaces are concentric, with a single porous spacer situated on or within a base plate that fixes and electrically insulates the first electrode from the second electrode.

Another embodiment of the invention is a method for focusing ions in a high field asymmetric waveform ion mobility spectrometry (FAIMS) device where one or more porous spacers are provided to address an analyzer region of the FAIMS cell and a focusing gas is delivered through the porous spacers to pneumatically focus ions traveling from an inlet to an outlet in the analyzer region of the FAIMS cell.

DETAILED DESCRIPTION OF THE INVENTION

Figure 1:
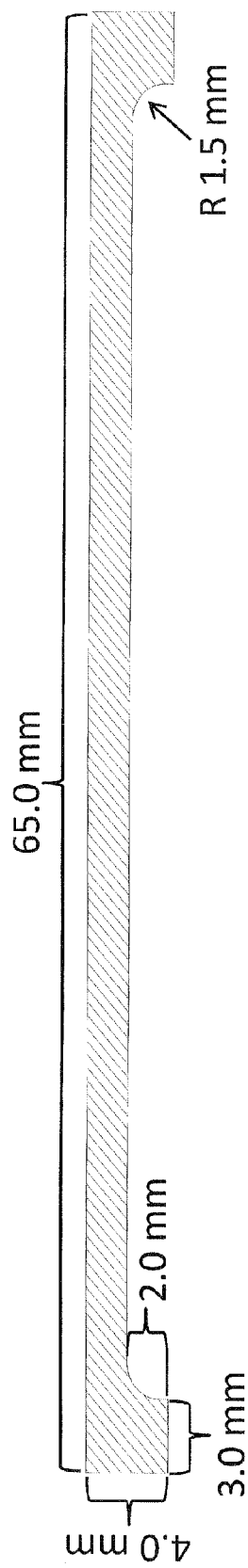
FIG. 1 shows a porous spacer for inclusion in a planar FAIMS cell according to an embodiment of the invention.

Embodiments of the invention are directed to FAIMS devices employing at least one porous nonconductive spacer through which focusing gas is passed for inhibition of lateral diffusion of ions in analyzer regions of FAIMS cells and a method of improving the ion transmission in FAIMS devices. FAIMS devices can be of the planar, cylindrical or partial ovoidal geometry, where the porous spacers are situated to counter diffusion toward non-electrode surfaces. The spacers can be porous due to the nature of the material being inherently porous, or by the structuring of the material as a mesh or including an array of holes that are machined or otherwise constructed through the spacer. Porous materials that can be used include: porous plastic, porous glass, sintered ceramic, sintered glass, microperforated anodized aluminum, and microperforated plastic. If a porous spacer is constructed of an electrically conductive material, the porous spacer must be electrically isolated from the electrodes. The porous spacer can be in communication with a channel that delivers a focusing gas to the spacer surface, external to the analyzer region or the entire device can be suspended in an atmosphere that is of higher pressure than that of the analyzer region such that focusing gas diffuses through the spacer into the analyzer region. The focusing gas flow through the spacer can vary, and a flow of less than 0.7 L/min to in excess of 1.4 L/min at a pressure of about 0.5 to 1.5 atmospheres is appropriate in many embodiments of the invention. The focusing gas flow rate is generally dictated by the curtain gas flow rate from the ion inlet through the analyzer region and out of the ion outlets to a detector, for example, into a mass spectrometer that often is coupled to the FAIMS device.

In many embodiments of the invention porous spacers and conduits and focusing gas sources are constructed to provide an even focusing gas flow over the entire gas exiting surface of the porous spacer. In some embodiments of the invention the focusing gas flow over different portions of the porous spacer is not uniform. The porous spacer can have different focusing gas pressures provided to different portions of the porous spacer, the porosity can vary for different portions of the porous spacer, and/or the effective thickness of the porous spacer can differ at different portions of the porous spacer to provide different focusing gas flows in to the analyzer region at different positions on the spacer. The various focusing gas pressures can be provided by the use of different focusing gas sources directed to a portion of the porous spacer or any geometry or number of conduits of one or more focusing gas sources to varied inlet sites along a porous spacer. The variation in focusing gas flow over the gas exiting surface of the porous spacer can be of any sort, for example, an decreasing or increasing gradient from the portions of the porous spacer near the ion inlet or inlets to the portions of the porous spacer near the ion outlet or outlets. The porous spacer can be a single unit or can be an ensemble of a plurality of segments. The focusing gas flow through a plurality of porous spacers or porous spacer segments can be independently adjusted to optimize the focusing of the ions in the analyzer region as they proceed to the ion outlet.

In embodiments of the invention, the focusing gas that flows through porous space can be any non-reactive gas, for example nitrogen, helium or other noble gas, carbon dioxide, sulfur hexafluoride or any combination thereof. In some embodiments of the invention, one or more reactive chemicals in the gas phase can be included. Reactive chemicals can include ammonia, acetone, methanol, benzene, toluene, chlorine compounds such as dichloromethane, or bromine compounds such as dibromomethane.

In one embodiment of the invention planar FAIMS cells have at least one ion inlet, where ions are delivered to an analyzer region. General structural features of a FAIMS cell are disclosed in Buryakov et al. *Int. J. Mass Spectrom, Ion Processes*, 128, 143 (1993) and incorporated herein by reference. In embodiments of the invention, the analyzer region is defined as the volume between two parallel plate electrodes that have a constant displacement between the opposing surfaces of the electrodes and two matched porous spacers, each situated and extending along the entire edge of opposite sides of the analyzer region that are parallel to the trajectory of the ion path to at least one ion outlet. Electrical contact is made to at least one of the electrodes for applying a compensation voltage between the electrodes and electrical contact is made to at least one of the electrodes for applying an asymmetric waveform to at least one of the electrodes. During application of the compensation voltage and the asymmetric waveform, ions are selectively transmitted through the analyzer region from one or more ion inlets to one or more ion outlets where a focusing gas flow is delivered through the porous spaces with equal pressure such that the focusing gas flow counters diffusion of ions perpendicular to the intended ion path from the ion inlet to the ion outlet. In this manner, the ions are pneumatically focused into a narrow trajectory to increase the proportion of ions that were introduced at the ion inlets that are delivered to the ion outlet. The pneumatic focusing allows for a significant increase of the ion transmission, with only a modest decrease in the resolving power.

An exemplary porous non-conductive spacer is illustrated in FIG. 1 for an analyzer region that is 65 mm from inlet to outlet where the two electrodes are separated by a distance of 1.5 mm. The spacer is 2.0 mm through the majority of the analyzer region but is 4.0 mm in thickness at the inlet and outlet ends extending 3.0 mm from these ends.

Figure 2:
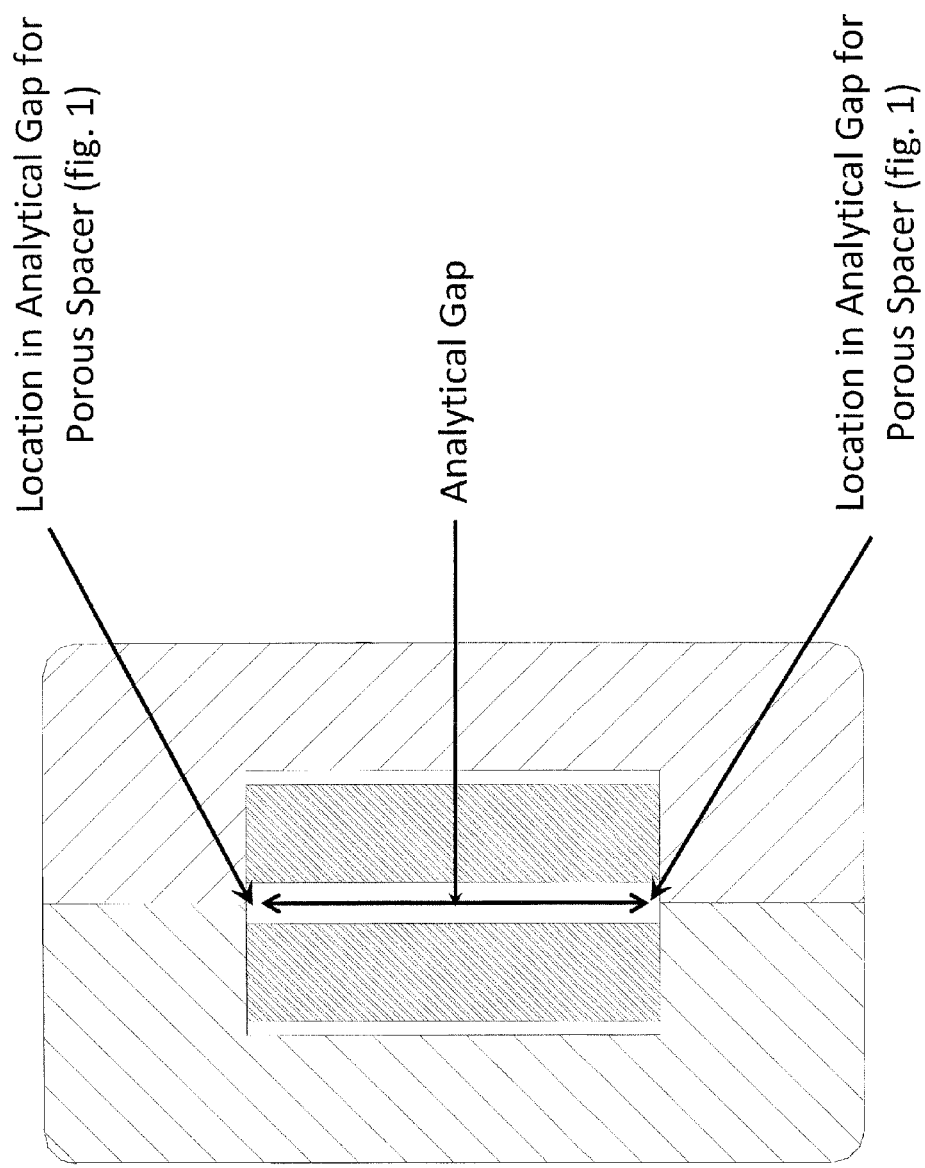
FIG. 2 shows the inlet to the analytical gap of a planar FAIMS cell according to an embodiment of the invention, where the porous spacers of FIG. 1 are situated as indicated on the two sides of the cell where the length of the spacer extends from the inlet (shown) to an outlet (not shown).

FIG. 2 shows a planar FAIMS cell at an inlet face according to an embodiment of the invention where a pair of ends of the porous non-conductive spacers and a pair of ends of the electrodes define the entrance to the analyzer region which extends from the ion inlet to the ion outlet, having a rectangular shape. In other embodiments of the invention, other geometries can be imposed by the actual inlet and outlet structures, and multiple inlets and/or outlets can be employed.

Figure 3:
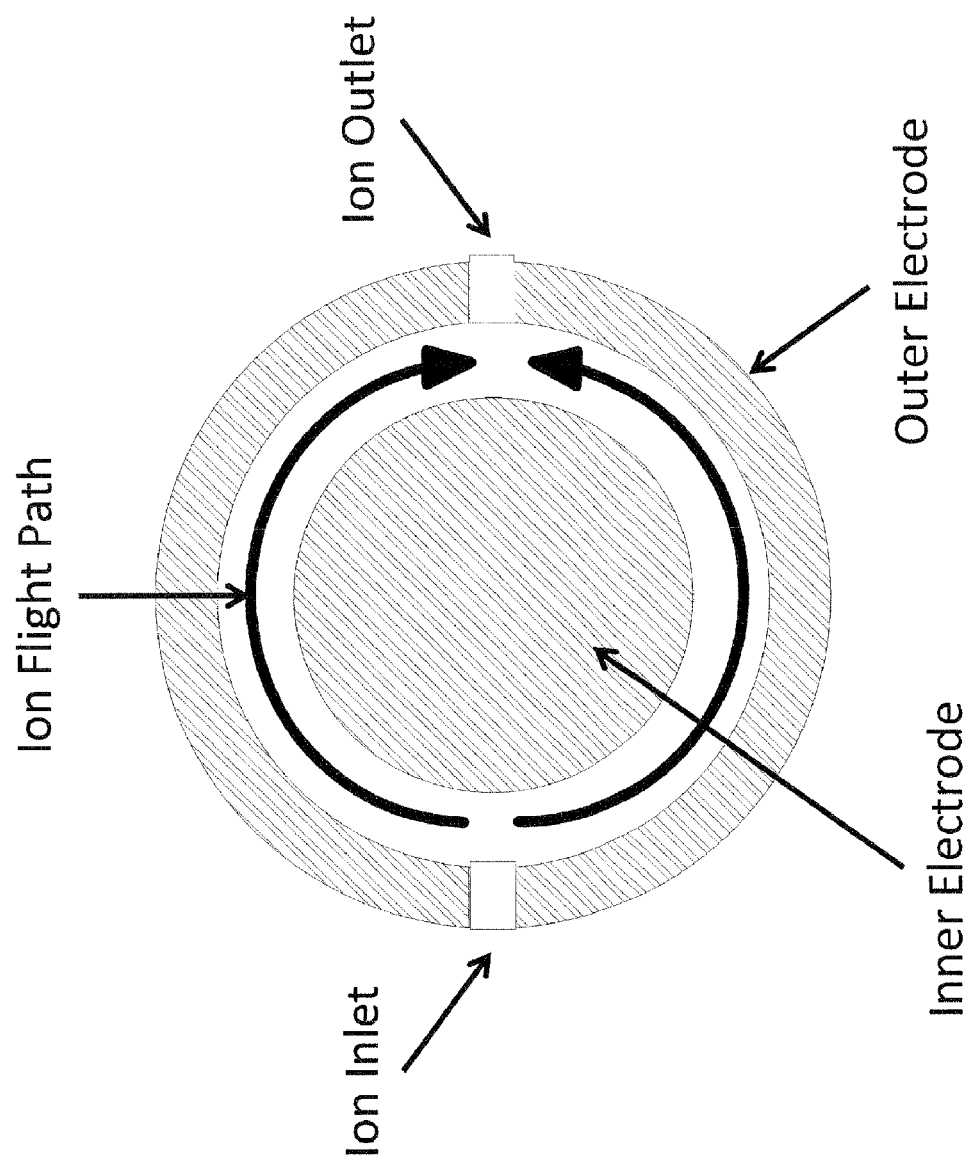
FIG. 3 shows a cross-section of the analyzer region of a "side-to-side" cylindrical FAIMS cell bounded by the inner and outer electrodes for ion trajectories from a single ion inlet to a single ion outlet as indicated by arrows.
Figure 4:
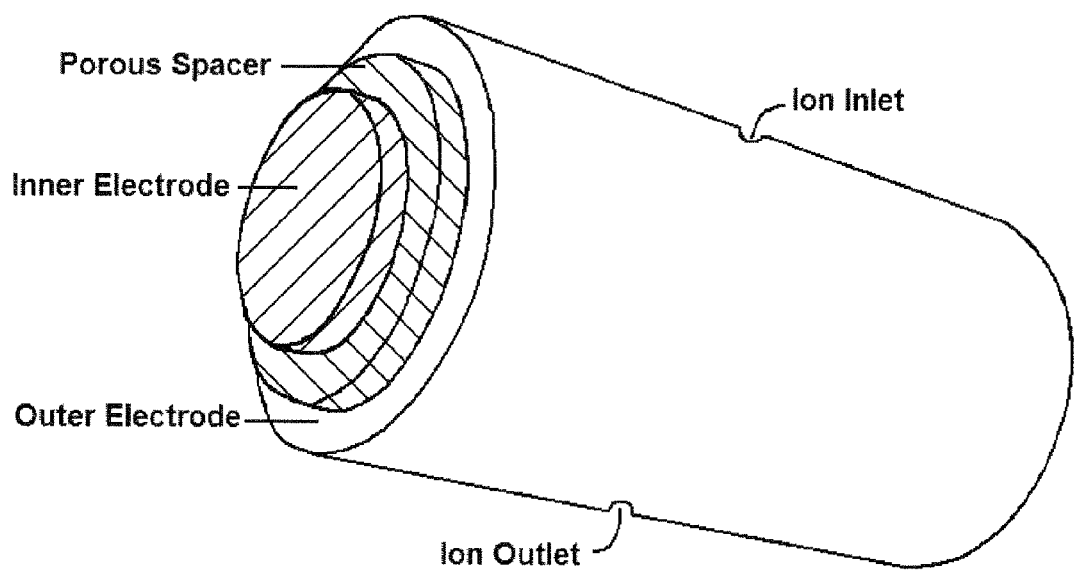
FIG. 4 shows a Exterior view of a "side-to-side" cylindrical FAIMS cell according to an embodiment of the invention where a pair of disk shaped porous spacers sandwich the analyzer region according to an embodiment of the invention.

In another embodiment of the invention, a "side-to-side" cylindrical FAIMS device where at least one ion inlet and at least one ion outlet are situated 180° from each other in opposite sides of an outer cylindrical electrode tube and the analyzer region is the space between the cylindrical tube electrode and cylindrical core electrode concentric to the electrodes and coplanar with the ion inlet and ion outlet. A cross-section of such a "side-to-side" cylindrical FAIMS cell at the analyzer region is shown in FIG. 3. The general geometry of a "side-to-side" FAIMS cell is disclosed in Guevremont et al., WO 1/69216 and is incorporated herein by reference. Ions travel around the inner cylinder (inner electrode) in the analyzer annular region between the ion inlet and ion outlet as illustrated in FIG. 3. Disk-shaped porous spacers are situated in the annular regions of the electrodes, on both sides of the analyzer region, to inhibit diffusion of ions perpendicular to the plane of the analyzer region between the central points of the inlet and outlet, as shown in FIG. 4, when a focusing gas is introduced through the porous spacers. In an embodiment of the invention, the focusing gas flow through the porous spacers of the cylindrical FAIMS cell can vary from that in the vicinity of the ion inlet to the vicinity of the ion outlet. In an embodiment of the invention, the focusing gas flow through the two porous spacers can be independently adjusted to focus the ions to the outlet.

In another embodiment of the invention a partial ovoidal FAIMS cell can be constructed where the portion of the base plate supporting the inner and outer electrodes can include a porous spacer. The general geometric features of a partial ovoidal FAIMS cell are disclosed in Prox et al. U.S. patent application Ser. No. 12/195,867 filed Aug. 21, 2008, and incorporated herein by reference. Losses by diffusion of ions into the base plate can be reduced by the use of a porous spacer on or incorporated into the base plate. The flow of focusing gas through the porous spacer can vary depending on the distance from the inlet and outlet. For example, a gradient can be established where the focusing gas flow is maximal in the vicinity of the inlet and minimal snear the outlet.

Materials and Methods

Samples

An analytical sample was prepared with 20 ppm trinitrotoluene (TNT) in nitrogen. Nitrogen was used as the curtain gas and the focusing gas.

Instrumentation

A FAIMS cell, as shown in FIG. 2, was constructed with stainless steel electrodes held in a polyetheretherketone (PEEK) body and porous non-conductive spacers. A dispersion voltage (DV) of −3800 V with a −1.3 kV curtain plate voltage was employed. A curtain gas flow of 2 L/min and a focusing gas flow of 0.942 L/min through the porous spacer with 0.663 L/min excess nitrogen removed annularly at the exit of the cell. The ions were generated by negative-ion atmospheric pressure chemical ionization (APCI) with a 4 microamps corona discharge, 250° C. vaporizer temperature, 25 microliter/min sample flow rate and 30 psi sheath gas pressure.

Results

Figure 5:
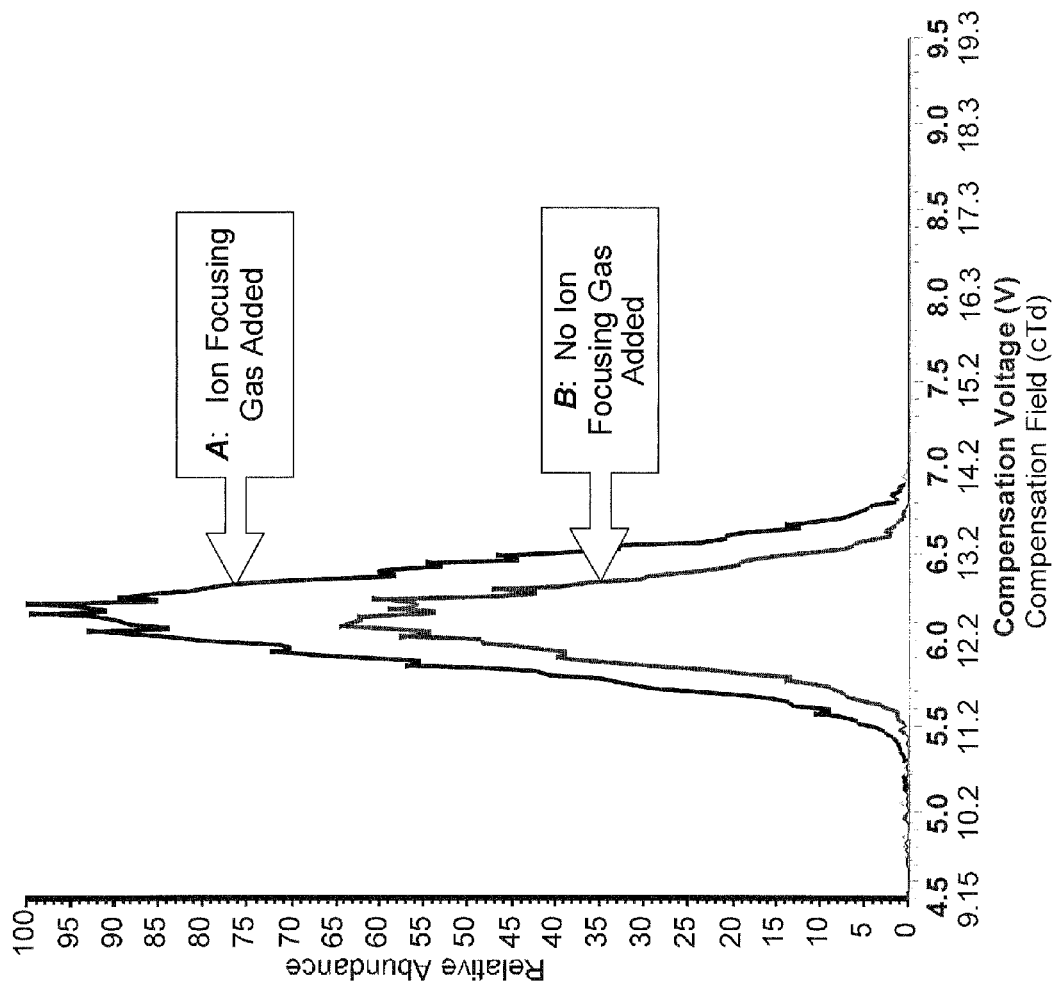
FIG. 5 shows analytical traces of a TNT sample using the type of FAIMS cell illustrated in FIG. 2 with the focusing gas flow on (top trace) and with the focusing gas flow off (bottom trace).

FIG. 5 shows output from the analysis of TNT using the FAIMS cell shown in FIG. 2 with (bottom trace) the pneumatic focusing gas turned off and on (top trace).

All patents, patent applications, provisional applications, and publications referred to or cited herein, supra or infra, are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

We claim:

1. An apparatus for separating ions, comprising:
   at least one ion inlet;
   at least one ion outlet;
   a first electrode comprising a surface;
   a second electrode comprising a surface;
   at least one porous spacer, wherein said first and second electrodes have a constant displacement between said surfaces of said first and second electrodes and electrical insulating said first electrode from said second electrode, wherein the volume between said surfaces and said at least one spacer define an analyzer region extending between said at least one ion inlet and said at least one ion outlet;
   an electrical contact on at least one of said first and second electrodes for applying a compensation voltage between said first and second electrodes, and an electrical contact on at least one of said first and second electrodes for applying an asymmetric waveform to at least one of said first and second electrodes wherein during application of said compensation voltage and said asymmetric waveform at least one ion is selectively transmitted through said analyzer region from said at least one ion inlet to said ion outlet; and
   at least one gas source providing a focusing gas for diffusion through said porous spacers wherein the ions are focused pneumatically by said focusing gas.

2. The apparatus of claim 1, wherein said porous spacers comprises a porous plastic, porous glass, sintered ceramic, sintered glass, microperforated anodized aluminum, or microperforated plastic.

3. The apparatus of claim 1, wherein said focusing gas comprises an inert gas, a reactive gas or a combination thereof.

4. The apparatus of claim 3, wherein said inert gas comprises nitrogen, helium, neon, argon, carbon dioxide, sulfur hexafluoride or any combination thereof.

5. The apparatus of claim 3, wherein said reactive gas comprises ammonia, acetone, methanol, benzene, toluene, dichloromethane, dibromomethane or any combination thereof.

6. The apparatus of claim 1, wherein said porous spacer has an effectively uniform porosity.

7. The apparatus of claim 1, wherein said porous spacer has a different porosity at different portions of said porous spacer.

8. The apparatus of claim 1, wherein said at least one gas source provides different focusing gas pressures at different portions of said porous spacer.

9. The apparatus of claim 1, wherein said porous spacer comprises an ensemble of porous spacer segments.

10. The apparatus of claim 9, wherein said porous spacer segments are independently addressable by said at least one gas source.

11. The apparatus of claim 1, wherein said surfaces of said first electrode and said second electrode are opposing, parallel and flat and a pair of said porous spacers are situated between said surfaces of said first electrode and said second electrode on opposing sides of said analyzer region.

12. The apparatus of claim 1, wherein said first electrode comprises an outer cylindrical surface and said second electrode comprises an inner cylindrical surface, said outer cylindrical surface coaxial to said inner cylindrical surface, and a pair of said porous spacers situated between said first electrode and said second electrode on opposing sides and parallel to said analyzer region.

13. The apparatus of claim 1, wherein said first electrode comprises an outer electrode comprising an inner concave partial ovoidal surface and said second electrode comprises an inner electrode comprising an outer convex partial ovoidal surface, said convex partial ovoidal surface concentric with said concave partial ovoidal surface, and said porous spacer situated on or within a base plate comprising a material wherein said first electrode and said second electrode are fixed and electrically insulated from each other.

14. A method for focusing ions in a high field asymmetric waveform ion mobility spectrometry (FAIMS) device comprising the steps of:
    providing at least one porous spacer that addresses an analyzer region of a FAIMS cell; and
    delivering a focusing gas through said porous spacer into said analyzer region, wherein ions passing from at least one ion inlet through said analyzer region to at least one ion outlet are pneumatically focused.

15. The method of claim 14, wherein said porous spacers comprises a porous plastic, porous glass, sintered ceramic, sintered glass, microperforated anodized aluminum, or microperforated plastic.

16. The method of claim 14, wherein said focusing gas comprises an inert gas, a reactive gas or a combination thereof.

17. The method of claim 16, wherein said inert gas comprises nitrogen, helium, neon, argon, carbon dioxide, sulfur hexafluoride or any combination thereof.

18. The method of claim 16, wherein said reactive gas comprises ammonia, acetone, methanol, benzene, toluene, dichloromethane, dibromomethane or any combination thereof.

19. The method of claim 14, wherein said porous spacer has an effectively uniform porosity.

20. The method of claim 14, wherein said porous spacer has a different porosity at different portions of said porous spacer.

* * * * *

UNITED STATES PATENT AND TRADEMARK OFFICE
CERTIFICATE OF CORRECTION

| | |
|---|---|
| PATENT NO. | : 8,049,167 B2 |
| APPLICATION NO. | : 12/723066 |
| DATED | : November 1, 2011 |
| INVENTOR(S) | : Leonard C. Rorrer, III et al. |

It is certified that error appears in the above-identified patent and that said Letters Patent is hereby corrected as shown below:

Column 2,
Lines 36-37, "effective reducing" should read --effectively reducing--.

Column 3,
Line 9, "can further diminishes the" should read --can further diminish the--.
Line 19, "it would be advantages to" should read --it would be advantageous to--.
Line 43, "spacer can be constricted of" should read --spacer can be constructed of--.

Column 6,
Line 49, "minimal snear the" should read --minimal near the--.

Signed and Sealed this
Sixth Day of March, 2012

David J. Kappos
*Director of the United States Patent and Trademark Office*